United States Patent [19]

Alkemade et al.

[11] Patent Number: 5,102,783

[45] Date of Patent: Apr. 7, 1992

[54] COMPOSITION AND METHOD FOR CULTURING AND FREEZING CELLS AND TISSUES

[75] Inventors: Stanley J. Alkemade, Seaforth; André Palasz; Reuben J. Mapletoft, both of Saskatoon, all of Canada

[73] Assignee: Vetrepharm, Inc., London, Canada

[21] Appl. No.: 464,428

[22] Filed: Jan. 12, 1990

[51] Int. Cl.$^5$ .................... A01N 1/02; C12N 5/06
[52] U.S. Cl. ........................ 435/1; 62/62; 62/78; 435/2; 435/240.2
[58] Field of Search ........... 435/240.3, 240.31, 1, 435/2, 240.2; 514/54; 62/62, 65

[56] References Cited

U.S. PATENT DOCUMENTS

| | | | |
|---|---|---|---|
| 3,708,575 | 1/1973 | Gottfried | 424/94 |
| 3,898,325 | 8/1975 | Revici | 424/94 |
| 3,945,889 | 3/1976 | Mima et al. | 195/62 |
| 4,038,139 | 7/1977 | Birch | 435/240.3 |
| 4,141,973 | 2/1979 | Balazs | 424/180 |
| 4,187,291 | 2/1980 | Marissal | 424/94 |
| 4,191,748 | 3/1980 | Holzmann | 424/94 |
| 4,272,522 | 6/1981 | Balazs | 424/94 |
| 4,303,676 | 12/1981 | Balazs | 424/359 |
| 4,512,337 | 4/1985 | Leveskis | 600/34 |
| 4,696,917 | 9/1987 | Lindstrom et al. | 514/54 |
| 4,746,504 | 5/1988 | Nimrod et al. | 424/1.1 |
| 4,780,414 | 10/1988 | Nimrod et al. | 435/101 |
| 4,784,990 | 11/1988 | Nimrod et al. | 514/54 |
| 4,784,991 | 11/1988 | Nimrod et al. | 514/62 |
| 4,801,619 | 1/1989 | Lindblad | 514/828 |
| 4,804,537 | 2/1989 | Bergman et al. | 424/105 |
| 4,808,576 | 2/1989 | Schultz et al. | 514/54 |
| 4,886,786 | 12/1989 | Lindstrom et al. | 514/54 |

OTHER PUBLICATIONS

Carson et al., Glycoconjugate Synthesis During Early Pregnancy: Hyaluronate Synthesis and Function, Biological Abstracts, vol. 83, No. 12, Ref. No. 123615.

*Primary Examiner*—John Doll
*Assistant Examiner*—George C. Elliott
*Attorney, Agent, or Firm*—Jones, Askew & Lunsford

[57] ABSTRACT

The present invention includes a composition and method for culturing and freezing cells and tissues without serum or serum products in the culture medium by substituting hyaluronic acid for the serum or serum products. The composition and method are especially well-suited for culturing and freezing embryos, ova and sperm. The present invention reduces the risk of transmittal of microorganisms such as viruses.

16 Claims, No Drawings

COMPOSITION AND METHOD FOR CULTURING AND FREEZING CELLS AND TISSUES

FIELD OF INVENTION

This invention relates in general to a composition and method for culturing and freezing cells and tissues and more particularly relates to a composition and method for harvesting, culturing and freezing embryos using a medium containing hyaluronic acid.

BACKGROUND OF THE INVENTION

The term "serum" as used herein means the liquid portion of the blood that remains after blood cells and fibrinogen/fibrin are removed. The term "plasma" as used herein means the liquid portion of blood that remains after blood cells are removed. The term "serum products" means any component of the serum, such as soluble proteins, lipids or carbohydrates or combinations thereof. An example of a serum protein is albumin.

The use of freezing techniques to freeze various cells and tissues for long term storage has become increasingly popular. In particular, the agricultural industry has successfully utilized these freezing techniques in animal husbandry. Furthermore, freezing techniques have been used to preserve ova, sperm and embryos from humans for later use.

A large industry is developing that is concerned with methods of fertilizing and transferring ova and embryos to surrogate females. The advantages of this technology to the animal husbandry industry include increasing the reproductive rate of valuable animals, decreasing the generation interval, increasing the number of progeny per female through controlled multiple births, and transporting embryos with selected genetic characteristics to distant places. This technology has been used for over 300 species including, but not limited to, cattle, swine, sheep, goats and other agriculture animals. The technology has also been used for freezing human embryos.

By way of example, a brief description of the biology of bovine reproduction follows: Bovine embryos move from the oviduct to the uterus four to five days after estrus (three to four days after ovulation), although in super ovulated cows, a few remain in the oviduct through day seven. A high percentage of embryos can usually be recovered nonsurgically from the uterus six or more days after the beginning of estrus.

Several procedures are currently available for recovering embryos. One such procedure comprises inserting a Rusch or Foley catheter through the cervix into the uterus by palpating through the wall of the rectum with one hand as is done for artificial insemination. The latex catheter usually consists of three channels for inflow, outflow, and inflation of the balloon-like cuff that prevents the escape of fluid after insertion. Each uterine horn is filled and emptied several times with 30–200 ml of fluid each time according to the size of the uterus. The embryos are flushed out with this fluid into large graduated cylinders. Embryos can be filtered with a 50–70$\mu$ mesh filter or allowed to settle for thirty minutes and can then be located under a stereo microscope by searching through an aliquot from the bottom of the cylinder. They are then stored in small containers or loaded into 0.25 to 5 ml straws until transferred.

In addition, the embryos can be recovered surgically. This is the procedure of choice for laboratory animals and for certain agricultural animals and may be the method of individual operator preference for large agricultural animals.

Embryos from the one cell to the early blastocyst stage (7 to 8 days after estrus) are between 120 and 140 micrometers in diameter exclusive of the zone of pellucida. Between days 8 and 10, they double in diameter, hatch from the zone of pellucida, and then grow to 20 cm or more in length by day 18. Since bovine embryos form no intimate attachment to the uterus before day 18, they can be recovered nonsurgically until this time, although they are increasingly prone to damage after day 14. It appears that a larger number of normal embryos can be obtained nonsurgically 6 to 8 days after estrus than at other times. (See U.S. Pat. No. 4,780,451.)

After the embryos are collected from the donor cow, they should be transferred to recipient animals within a short period of time. Alternatively, the embryos can be cooled to refrigerator temperatures or frozen. Conventional freezing media contain some type of serum. For example, newborn calf serum or bovine serum albumin (BSA) plus additional glycerol and/or other constituents have been widely used in media for embryo freezing as both cryoprotectants and surfactants.

However, these sera have a major problem in that they can transfer viral contaminants to the embryo including, but not limited to, bovine virus diarrhea (BVD), infectious bovine rhinotrachitis (IBR), bovine spongiform encephalopathy (BSE), Scrapie, blue tongue, and foot and mouth disease. In addition, serum from animals inherently adds undefined components to the freezing media allowing for the possibility of deleterious effects on the embryos.

There is accordingly a need for a composition and method for culturing and freezing living tissues and cells, including embryos, which do not contain serum or serum products from animals. There is also a need for a culturing and freezing medium which is completely defined and does not contain any serum or serum products from animals or humans. The freezing medium should protect the living tissue or cells that are being frozen and allow high viability of the cells or tissue when they are thawed.

SUMMARY OF THE INVENTION

The present invention comprises a composition and method for culturing and freezing cells or tissues comprising a culture solution containing the nutritional substances necessary to support the cells or tissues and hyaluronic acid in a concentration effective to be a substitute for serum or serum products. Various types of cells or tissues that could be frozen using a conventional freezing medium containing hyaluronic acid include, but are not limited to, embryos, unfertilized ova or sperm.

The present invention also includes flushing media for flushing or washing ova or embryos from the reproductive tract, oviducts or uterus, of a female. The medium contain hyaluronic acid in place of serum or other serum products. In addition, the present invention includes growth media which contains hyaluronic acid. This growth medium can be used to allow the embryo to grow before it is transferred or frozen.

The preferred molecular weight of the hyaluronic acid contained in the freezing medium is between approximately $1.0 \times 10^4$ and $3 \times 10^6$ Daltons. The more preferred molecular weight of the hyaluronic acid is between approximately $5 \times 10^5$ to $1.2 \times 10^6$ Daltons. The most preferred molecular weight of the hyaluronic acid as used in the present invention is $7.5 \times 10^5$ Daltons.

The concentration of hyaluronic acid in the culture and freezing media of the present invention is between approximately 0.01 and 10 mg/ml. A preferred concentration of hyaluronic acid is between approximately 0.05 and 5 mg/ml with a more preferred concentration being between approximately 0.5 mg/ml to 2 mg/ml. A most preferred concentration of hyaluronic acid is approximately 1.0 mg/ml.

Accordingly, it is an object of the present invention to provide an effective composition and method for culturing and freezing cells and tissues and for maintaining their viability after thawing.

It is another object of the present invention to provide a medium for flushing ova or embryos from a female.

It is another object of the present invention to provide a culture and freezing medium that will reduce or eliminate the transfer of microorganisms, such as viruses, to the cells and tissues during the freezing process.

It is another object of the present invention to provide a medium that does not contain serum albumin.

It is yet another object of the present invention to provide a medium for freezing embryos, ova and sperm.

It is yet another object of the present invention to provide a medium that is completely defined for freezing living cells and tissues.

It is yet another object of the present invention to avoid deleterious effects on living cells and tissues being frozen.

It is yet another object of the present invention to increase the reproductive capability of female cows.

It is a further object of the present invention to produce superior agriculture animals, including but not limited to, cattle, swine, horses, sheep, deer and goats.

It is a further object of the present invention to produce superior laboratory animals including, but not limited to, rats, mice, guinea pigs and rabbits.

It is a further object of the present invention to provide a flushing, culturing and freezing medium for culturing and freezing human ova, sperm and embryos that does not contain serum, serum albumin or other blood products including plasma.

It is yet another object of the present invention to provide a culture medium capable of extending the useful life of embryos in vitro.

It is another object of the present invention to provide a medium for the culturing and freezing of human embryos, ova and sperm.

Other objects and advantages of the present invention will become more readily apparent from the following description of a preferred embodiment.

DETAILED DESCRIPTION OF PREFERRED EMBODIMENTS

The present invention includes a composition for culturing and freezing cells or tissues comprising a solution containing the nutritional substances necessary to support the cells or tissues and hyaluronic acid in a concentration effective to be a substitute for serum or serum products.

The present invention also includes a method for culturing cells or tissues comprising the step of mixing the cells or tissues with a medium, the medium comprising a culture solution containing the nutritional substances necessary to support the cells or tissues and hyaluronic acid in a concentration effective to be a substitute for serum or serum products.

The present invention also includes a method for freezing cells or tissues comprising the steps of (a) mixing the cells or tissues with a medium, the medium comprising a culture solution containing the nutritional substances necessary to support the cells or tissues and hyaluronic acid in a concentration effective to be a substitute for serum or serum products; and (b) lowering the temperature of the culture medium sufficiently to preserve the embryos in a viable condition.

The present invention further includes a method for flushing ova or embryos from a donor female comprising the step of flushing the reproductive tract, oviduct or uterus, of an appropriate female with a medium, the medium comprising a culture solution containing the nutritional substances necessary to support the cells or tissues and hyaluronic acid in a concentration effective to be a substitute for serum or serum products.

The hyaluronic acid is a substitute for serum or serum products. The culture and freezing medium may be any conventional medium, such as Dulbecco's phosphate buffered saline or Ham's F-10 medium. According to the present invention, hyaluronic acid can replace serum in conventional culture and freezing media thereby reducing or eliminating the risk of transfer of harmful microorganisms such as viruses which may be present in the serum.

The basic culture media are well known to those of ordinary skill in the art. These media include a solution containing substances which are osmotically compatible with the cells and/or tissues which are placed in the media and, for long term culture, these media also contain substances which are nutritionally necessary to support the cells and/or tissues.

The present invention is particularly useful in the culturing and freezing of embryos. The media which comprise the present invention may either be used simply as a collection material to flush the embryo from the reproductive tract of an animal and to hold the embryo after it has been flushed from the donor animal or they may be used to preserve the embryo for an extended period of time. If the culture medium of the present invention is used for an extended period of time, it may be frozen with the embryo by the addition of a cryopreservation agent, including but not limited to, glycerol or dimethyl sulfoxide. In addition, the media which comprise the present invention may be used to culture the embryo to allow it to grow before transfer to the recipient female. It is to be understood that the present invention can be used equally well for both animal embryos or human embryos, as well as for ova and sperm.

Hyaluronic acid occurs in vitreous humor, synovial fluid (lubricating fluid of the joints), skin, umbilical cord, hemolytic streptococci Type A and C, pathologic joints and rooster combs. It is part of the gel-like ground substance of connective tissues and serves as a shock absorbent and lubricant. It occurs both free as the anion with simple cations or it can be associated with protein cations in a variety of tissues. In these tissues, the compound acts as a cement and a permeability barrier by allowing passage of metabolites but blocking invasion by bacteria.

Heretofore, hyaluronic acid has been used in many therapeutic applications. U.S. Pat. No. 4,141,973 to Balazs discloses the replacement of vitreous humor with hyaluronic acid during ophthalmic surgical procedures. Hyaluronic acid is also used as a antimicrobial agent (U.S. Pat. No. 4,784,991 to Nimrod); in cosmetic preparations (U.S. Pat. No. 4,187,291 to Marissal and U.S. Pat. No. 4,303,676 to Balazs); as a treatment for anesthesia (U.S. Pat. No. 3,898,329 to Revia) and as a treatment for inflammation of skeletal joints to Linblad (U.S. Pat. No. 4,801,619).

The hyaluronic acid molecule is a highly charged polyanion composed of alternating units of D-glucuronic acid and 2-acetamido-2-deoxy-D-glucose (see Meyer, K., Fed. Proc. 17:1075 (1958)); and Laurent, T. C., in: Chemistry and Molecular Biology of the Intercellular Matrix II. E. A. Balazs, ed. Academic Press, London and New York, pp. 703-712, (1970). These unbranched, elongated polysaccharide chains can be chemically crosslinked to produce sheets or microfilms of a water-insoluble, hydrophilic sodium hyaluronate membrane which maintains the large negative electrostatic potential and permeability of the uncrosslinked molecules.

The preferred form of hyaluronic acid in the present invention is the sodium salt of hyaluronic acid. It is to be understood that other soluble salt forms or the acid form of hyaluronic acid can be used to practice the present invention. It is not considered critical in the present invention which salt form is used. Salts that could be used include, but are not limited to, sodium potassium, ammonium and lithium.

The preferred molecular weight fraction of hyaluronic acid encompasses polysaccharide chains composed of a repeating disaccharide unit consisting of sodium glucuronate and N-acetylglucosamine, linked by a $\beta 1 \rightarrow 3$ glycosidic bond. The disaccharide units are linked by $\beta 1 \rightarrow 4$ glycosidic bonds, to form linear chains of a defined average length. These polymer chains form random coils in solution, characterized by an extensive hydration volume. In aqueous solution at physiological pH and ion strength, these solutions are highly viscous with viscoelastic properties.

The hyaluronic acid fraction used in the present invention is produced from the combs of freshly slaughtered cocks. It is to be understood that other sources of hyaluronic acid can be used to obtain the preferred molecular weight fraction of hyaluronic acid. One production process consists of solvent extraction, followed by enzymatic digestion of contaminating protein. The resulting material is purified by molecular filtration and specific fractionation, followed by precipitation, washing and isolation of the active substance as the sodium salt.

Other sources of hyaluronic acid include, but are not limited to, microorganisms, umbilical cords and synthesized molecules.

The preferred molecular weight of the hyaluronic acid contained in the culture and freezing medium of the present invention is between approximately $1.0 \times 10^4$ and $3 \times 10^6$ Daltons. The more preferred molecular weight of the hyaluronic acid is between approximately $5 \times 10^5$ to $1.2 \times 10^6$ Daltons. The most preferred molecular weight of the hyaluronic acid as used in the present invention is $7.5 \times 10^5$ Daltons.

The concentration of hyaluronic acid in the culture and freezing medium of the present invention is between approximately 0.01 and 10 mg/ml. A preferred concentration of hyaluronic acid is between approximately 0.05 and 5 mg/ml with a more preferred concentration of hyaluronic acid in the medium between approximately 0.5 mg/ml to 2 mg/ml. A most preferred concentration is approximately 1.0 mg/ml.

There are a variety of culture media that can be used in practicing the present invention. One of the most common media for the collection and freezing of embryos is Dulbecco's phosphate buffered saline (D-PBS) solution incorporating 1% to 10% fetal calf serum, new born calf serum or steer serum. If the embryos are to be kept in an embryo culture medium for a substantial period of time, the D-PBS is normally supplemented with 10% to 20% serum. Alternatively, the embryo culture medium may consist of another known medium, Ham's F-10 containing serum or specifically bovine serum albumin. Other media include but are not limited to, B. W. W. (Brinster's, (Whitten's & Biggar's & Whittingham's medium) and normal saline. All of these media are commercially available from a variety of sources. These products are generally supplied in powder form and made up into an aqueous medium prior to receiving the embryos.

Normally, the above mentioned culture media can be used as a freezing media by adding a cryoprotectant, e.g., 10% glycerol, an energy source, e.g., glucose/pyruvate, antibiotics and in some cases a surfactant. In addition, a surfactant, such as poloxamer 188, can be added to the medium to retard the sticking of cells to the culture vessel. The preferred concentration of the surfactant is between 0.05 mg/ml to 10 mg/ml with a most preferred concentration of surfactant of between 0.1 mg/ml and 1 mg/ml.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

A freezing medium is prepared in Dulbecco's phosphate-buffered saline (Gibco Laboratories, Inc., Burlington Ontario) supplemented with glucose-pyruvate, antibiotics, 10% glycerol and 0.1% hyaluronic acid (1 mg/ml) or 20% newborn calf serum as indicated. The medium has the following formula:

| Dulbecco's PBS | |
|---|---|
| Na hyaluronate or | 1 mg/ml |
| Newborn calf serum | 20% |
| Glucose | 1 g/L |
| Na pyruvate | 40 mg/L |
| Sodium penicillin | 100,000 units/L |
| Streptomycin sulfate | 100,000 μg/L |
| Amphotericine B | 250 μg/L |
| Glycerol | 10% wt/vol. |

Mouse morulae are collected on day 2.5 (vaginal plug=day 0) from CDI 3-week old mice. The embryos are washed three times in a phosphate-buffered saline solution supplemented with hyaluronic acid or newborn calf serum as indicated. Embryos are equilibrated at room temperature for ten minutes in the freezing medium with hyaluronic acid or with newborn calf serum as indicated, the loaded onto 0.25 ml straws. The straws are seeded at $-7°$ C. and cooled at $0.5°$ C./min. and submerged into liquid nitrogen at $-35°$ C.

After two weeks, the embryos are then thawed in a 22° C. water-bath with mild agitation for one minute. Glycerol is diluted in a single step with 1.0M sucrose for ten minutes. After three washes in phosphate-buffered saline, the mouse embryos are placed in a modified Brinster's, Whitten's and Biggar's and Whittingham's culture medium (Gibco Laboratories, Burlington, Ontario) containing 0.4% bovine serum albumin, under paraffin oil and in a humidified atmosphere of 5% $CO_2$ in air at 37° C.

After 48 hours in culture, 84 of the 106 embryos (79.2%) frozen in the medium containing hyaluronic acid developed to expanded or hatched blastocysts (See Table I).

EXAMPLE II

A freezing medium is prepared in Dulbecco's phosphate-buffered saline culture medium containing glucose-pyruvate, antibiotics, 10% glycerol and 0.1% hyaluronic acid (1 mg/ml) or 20% newborn calf serum as indicated. A total of fifty-nine seven day bovine embryos (morulae to blastocyst) are collected and washed seven times in phosphate-buffered solution with hyaluronic acid or newborn calf serum as indicated. The bovine embryos are equilibrated in the freezing medium at room temperature for ten minutes and then loaded onto 0.25 ml straws. The straws are seeded at −7° C., cooled at 0.5° C./min. and then plunged at −35° C. into liquid nitrogen.

After two weeks the embryos are then thawed at 22° C. in air for five minutes. Glycerol is diluted in a single step with 1.0M sucrose for ten minutes. The embryos are washed three times in phosphate-buffered solution, then placed in Ham's F-10 (Gibco Laboratories, Burlington, Ontario) culture medium containing 0.4% bovine serum albumin under paraffin oil and in a humidified atmosphere of 5% $CO_2$ in air at 37° C.

After forty-eight hours in culture, 67.7% of the bovine embryos frozen in the medium containing hyaluronic acid developed to expanded or hatched blastocysts.

Table 1 summarizes the results of the two experiments described in Example I and II in which mouse and bovine embryos are frozen in a medium containing hyaluronic acid or newborn calf serum as indicated.

TABLE 1

| | Total No. of Embryos | No. Embryos developed | % Survival rate |
|---|---|---|---|
| Cattle/NCS | 61 | 41 | 67.2 |
| Cattle/HA | 59 | 40 | 67.7 |
| Mouse/NCS | 101 | 85 | 84.1 |
| Mouse/HA | 106 | 84 | 79.2 |

As can be seen in Table 1, the freezing medium containing hyaluronic acid is as effective in maintaining viability of the embryos as the freezing medium containing newborn calf serum.

EXAMPLE III

A determination is made of which molecular weight hyaluronic acid is most effective in terms of survival rate of the mouse embryos. The details of this experiment are set forth below.

The freezing medium described in Example 1 is prepared using hyaluronic acid of three different molecular weights to determine if the molecular weight of hyaluronic acid would affect embryo survival rates. Seventy-six embryos are frozen in a freezing medium containing hyaluronic acid (HA1) with a molecular weight of less than $3 \times 10^5$ Daltons (Molecular weight of the hyaluronic acid varies from approximately $3 \times 10^4$ to approximately $2.5 \times 10^5$ Daltons). Fifty eight embryos are frozen in a freezing medium with hyaluronic acid of a molecular weight of approximately between $5 \times 10^5$ and $7.5 \times 10^5$ Daltons (HA2). Sixty-seven embryos are frozen in a freezing medium with hyaluronic acid of a molecular weight approximately greater than $1.2 \times 10^6$ Daltons (HA3

The embryos are frozen and thawed by the same method described in Example 1. Table 2 shows the survival rates for the embryos.

TABLE 2

| | Total No. of Embryos | No. Embryos Developed | % Survival Rate |
|---|---|---|---|
| HA1 | 76 | 14 | 18.6 |
| HA2 | 58 | 51 | 87.9 |
| HA3 | 67 | 62 | 92.5 |

As shown in Table 2, the hyaluronic acid that has a molecular weight greater than 500,000 Daltons produced a survival rate greater than 87.9% while the hyaluronic acid that has a molecular weight less than 300,000 Daltons has a survival rate of only 18.6%.

It should be understood, of course, that the foregoing relates only to a preferred embodiment of the present invention and that numerous modifications or alterations may be made therein without departing from the spirit and the scope of the invention as set forth in the appended claims.

What is claimed is:

1. A composition for freezing cells or tissues comprising a solution containing the nutritional substances necessary to support the cells or tissues and hyaluronic acid having an average molecular weight of not less than approximately $2 \times 10^5$ Daltons in a concentration effective to be a substitute for serum or serum products.

2. The serum-free medium of claim 1, wherein the hyaluronic acid has an average molecular weight of between approximately $5 \times 10^5$ to $1.2 \times 10^6$ Daltons.

3. The serum-free medium of claim 1, wherein the hyaluronic acid has an average molecular weight of approximately $7.5 \times 10^5$ Daltons.

4. The serum-free medium of claim 1, wherein the cells are embryos.

5. The serum-free medium of claim 1, wherein the cells are unfertilized ova.

6. The serum-free medium of claim 1 wherein the cells are sperm.

7. The serum-free medium of claim 1, wherein the medium further comprises an effective amount of surfactant.

8. The serum-free medium of claim 7, wherein the surfactant is poloxamer 188.

9. A method for freezing animal cells or tissues comprising the steps of:
   a. mixing animal cells or tissues with a medium, the medium comprising a solution containing the nutritional substances necessary to support the cells or tissues and hyaluronic acid having an average molecular weight of more than $2 \times 10^5$ Daltons in a concentration effective to be a substitute for serum or serum products; and
   b. lowering the temperature of the medium sufficiently to preserve the animal cells or tissues in a viable condition.

10. The method of claim 9, wherein the hyaluronic acid has an average molecular weight of between approximately $5 \times 10^5$ to $1.2 \times 10^6$ Daltons.

11. The method of claim 9, wherein the hyaluronic acid has an average molecular weight of approximately $7.5 \times 10^5$ Daltons.

12. The method of claim 9, wherein the cells are embryos.

13. The method of claim 9, wherein the cells are unfertilized ova.

14. The method of claim 9, wherein the cells are sperm.

15. The method of claim 9, wherein the medium further comprises an effective amount of surfactant.

16. The method of claim 15 wherein the surfactant is poloxamer 188.